(12) United States Patent
Godfrey et al.

(10) Patent No.: US 8,656,909 B2
(45) Date of Patent: Feb. 25, 2014

(54) NOZZLE FOR A NASAL INHALER

(75) Inventors: James William Godfrey, Ware (GB); Mark Graham Hedley, Ware (GB)

(73) Assignee: Glaxo Group Limited, Brentford, Middlesex (GB)

( * ) Notice: Subject to any disclaimer, the term of this patent is extended or adjusted under 35 U.S.C. 154(b) by 0 days.

(21) Appl. No.: 13/167,200

(22) Filed: Jun. 23, 2011

(65) Prior Publication Data

US 2011/0253752 A1 Oct. 20, 2011

Related U.S. Application Data

(63) Continuation of application No. 11/996,768, filed as application No. PCT/GB2006/002792 on Jul. 27, 2006, now abandoned.

(30) Foreign Application Priority Data

Jul. 28, 2005 (GB) .................................. 0515592.4

(51) Int. Cl.
| | |
|---|---|
| *A62B 9/00* | (2006.01) |
| *A61M 16/20* | (2006.01) |
| *B05B 1/26* | (2006.01) |
| *B05B 1/34* | (2006.01) |
| *B05B 1/30* | (2006.01) |

(52) U.S. Cl.
USPC ............ 128/200.18; 128/200.24; 128/204.18; 128/204.25; 239/468

(58) Field of Classification Search
USPC ............ 128/200.11–200.24, 203.12, 203.15, 128/204.25; 239/302, 337, 333, 487, 489, 239/490, 482, 483, 488; 222/402.1; 604/151, 207, 211, 131, 209, 232, 208
See application file for complete search history.

(56) References Cited

U.S. PATENT DOCUMENTS 2,409,371 A * 10/1946 Mart .............................. 239/490
3,949,939 A    4/1976 Brown
(Continued)

FOREIGN PATENT DOCUMENTS

DE    20102271 U1   5/2001
EP    0166552 A2    1/1986
(Continued)

*Primary Examiner* — Annette Dixon
(74) *Attorney, Agent, or Firm* — James P. Riek

(57) ABSTRACT

A nozzle, for use in a fluid dispensing device, having a body defining a fluid flow channel which is shaped to impart acceleration and angular momentum to fluid passing therethrough, an inlet port formed in the body and defining an inlet to the channel, and an outlet port formed in the body and defining an outlet from the channel, wherein the fluid flow channel includes a swirl chamber having a plurality of swirl chamber segments, the swirl chamber being located between the channel inlet and the channel outlet, wherein the body is comprised of a mating assembly of a plurality of like component parts, each of the component parts providing one of the swirl chamber segments; wherein the fluid flow channel includes a plurality of inlets to the swirl chamber for feeding fluid into the swirl chamber and wherein each of the component parts provides one of the swirl chamber inlets; wherein the swirl chamber inlets are positioned to feed fluid into respectively different swirl chamber segments and wherein the swirl chamber segments are fed from one of the swirl chamber inlets provided by another of the component parts; and wherein each swirl chamber inlet is connected to the channel inlet by separate branches of the fluid flow channel.

20 Claims, 7 Drawing Sheets

(56) References Cited

U.S. PATENT DOCUMENTS

| | | | |
|---|---|---|---|
| 4,480,768 A | 11/1984 | Martin | |
| 4,624,413 A | 11/1986 | Corsette | |
| 4,801,093 A * | 1/1989 | Brunet et al. | 239/490 |
| 4,896,832 A | 1/1990 | Howlett | |
| 4,946,069 A | 8/1990 | Fuchs | |
| 4,961,727 A | 10/1990 | Beard | |
| 5,143,298 A | 9/1992 | Prokopoff | |
| 5,224,471 A | 7/1993 | Marelli | |
| 5,224,651 A | 7/1993 | Stahl | |
| 5,234,166 A | 8/1993 | Foster et al. | |
| 5,234,167 A | 8/1993 | Martin | |
| 5,284,132 A | 2/1994 | Geier | |
| 5,289,818 A | 3/1994 | Citterio et al. | |
| 5,309,900 A | 5/1994 | Knoch et al. | |
| 5,310,092 A | 5/1994 | Targell | |
| 5,323,936 A | 6/1994 | Wolter et al. | |
| 5,397,060 A | 3/1995 | Maas et al. | |
| 5,431,155 A | 7/1995 | Marelli | |
| 5,439,178 A | 8/1995 | Peterson | |
| 5,547,132 A | 8/1996 | Grogan | |
| 5,549,249 A | 8/1996 | Foster et al. | |
| 5,590,835 A | 1/1997 | Rosenthal et al. | |
| 5,628,461 A | 5/1997 | Foster et al. | |
| 5,769,325 A | 6/1998 | Jouillat et al. | |
| 5,855,322 A | 1/1999 | Py | |
| 5,860,416 A | 1/1999 | Howlett | |
| 5,860,602 A | 1/1999 | Tilton et al. | |
| 5,931,386 A | 8/1999 | Jouillat | |
| 5,934,555 A | 8/1999 | Dobbeling et al. | |
| 6,050,504 A | 4/2000 | Schultz et al. | |
| 6,186,141 B1 | 2/2001 | Pike et al. | |
| 6,257,457 B1 | 7/2001 | Oechsel | |
| 6,418,925 B1 | 7/2002 | Genova et al. | |
| 6,443,370 B1 | 9/2002 | Brulle et al. | |
| 6,503,362 B1 | 1/2003 | Bartels et al. | |
| 7,484,678 B2 * | 2/2009 | Morrison | 239/302 |
| 2001/0011687 A1 | 8/2001 | Benoist | |

FOREIGN PATENT DOCUMENTS

| | | |
|---|---|---|
| EP | 0237696 A2 | 9/1987 |
| EP | 0412524 A1 | 2/1991 |
| EP | 0598237 A2 | 5/1994 |
| EP | 0706830 A1 | 4/1996 |
| FR | 2622478 A1 | 11/1987 |
| WO | 8502562 A1 | 6/1985 |
| WO | 8901365 A1 | 2/1989 |
| WO | 9629108 A1 | 9/1996 |
| WO | 9731841 A1 | 9/1997 |
| WO | 0058014 A1 | 10/2000 |
| WO | 0136033 A2 | 5/2001 |
| WO | 0158508 A2 | 8/2001 |
| WO | 03015929 A1 | 2/2003 |
| WO | 2004020111 A1 | 3/2004 |
| WO | 2004022241 A2 | 3/2004 |
| WO | 2004043609 A1 | 5/2004 |
| WO | 2004054722 A1 | 7/2004 |
| WO | 2004054723 A1 | 7/2004 |
| WO | 2004062813 A1 | 7/2004 |
| WO | 2004076072 A1 | 9/2004 |
| WO | 2004094068 A2 | 11/2004 |
| WO | 2005005055 A1 | 1/2005 |

* cited by examiner

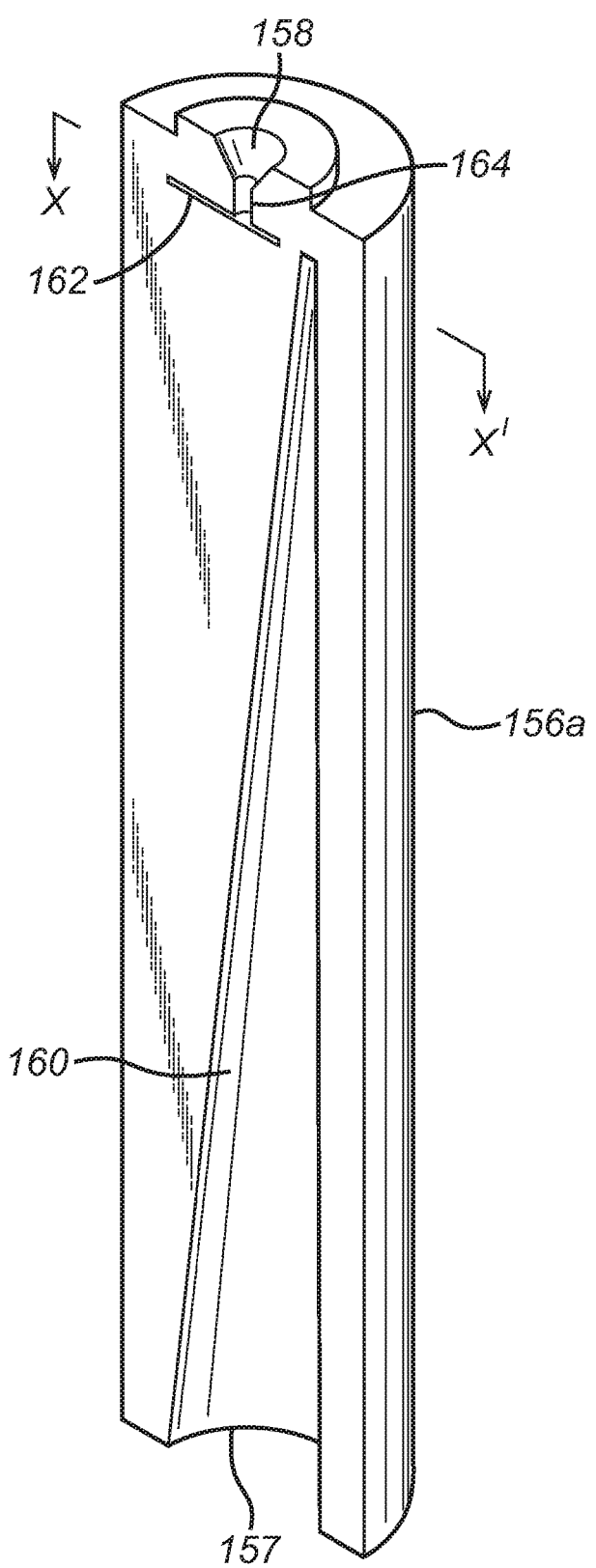

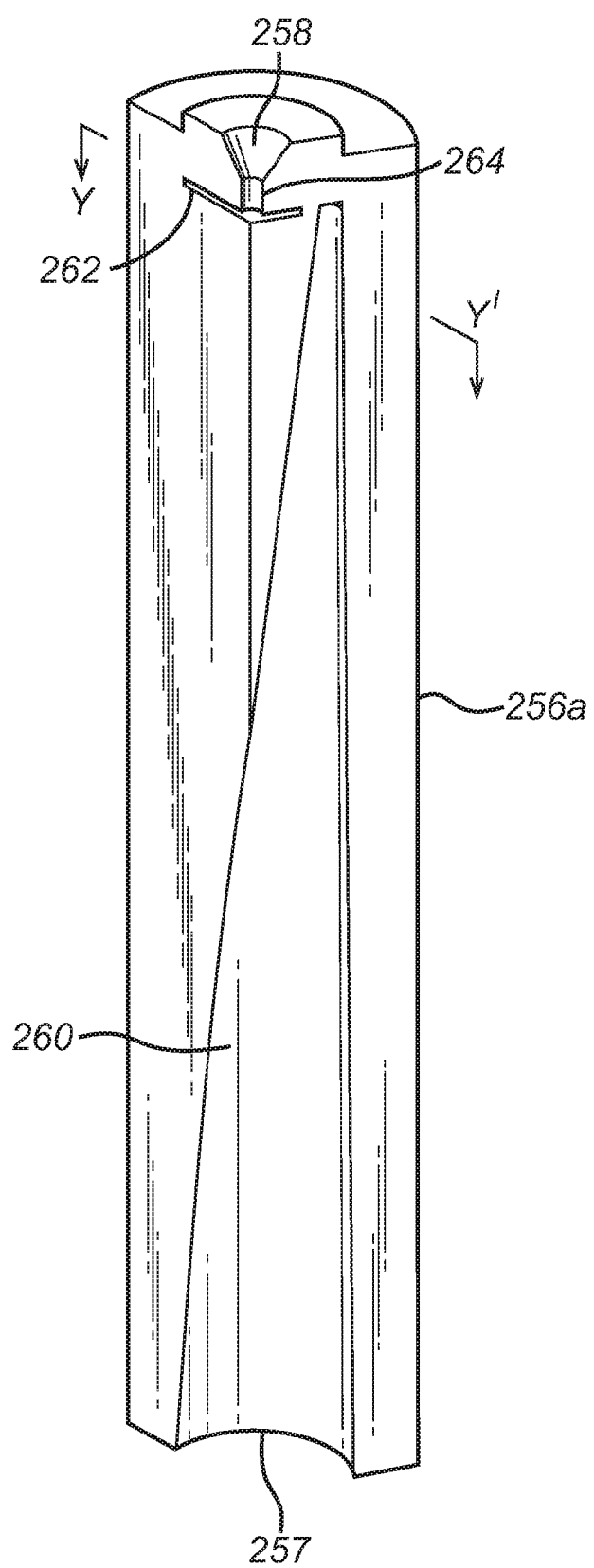

NOZZLE FOR A NASAL INHALER

CROSS-REFERENCE TO RELATED APPLICATIONS

The present application is a continuation application of U.S. patent application Ser. No. 11/996,768 filed on 25 Jan. 2008, now abandoned, pursuant to 35 USC §371 as a United States National Phase Application of International Patent Application No. PCT/GB2006/002792 filed on 27 Jul. 2006, which claims priority from GB 0515592.4 filed on 28 Jul. 2005 in the United Kingdom.

FIELD OF THE INVENTION

The present invention relates to a nozzle for use with a fluid dispensing device for nasal administration of medicament.

BACKGROUND OF THE INVENTION

It is well known to provide a medicament dispenser device in which a fluid medicament formulation is dispensed as a spray via a nozzle to the nasal cavity of a user. In general, the fluid is delivered to the nozzle upon the application of user force to a fluid pumping mechanism. Such nasal dispensers may be arranged to dispense a single dose or may alternatively be arranged with a fluid reservoir from which individual metered doses may be pumped. A general example of such a pump action nasal inhaler device is shown and described in U.S. Pat. No. 4,946,069.

It is a problem with such pump action nasal spray devices that the characteristics of the spray are to an extent dependent upon the manner of actuation by the user. If the user actuates the device in a slow or lethargic manner then the dispensing of the fluid may be less spray-like than required for effective delivery to the nasal cavity. If the rate of discharge is too low full atomisation may not occur and the spray undesirably comprises of relatively large droplets of fluid. In extreme cases, no spray is produced and the fluid simply dribbles out from the tip of the nozzle.

To improve spray characteristics, it is known to be advantageous to provide a feature to the nozzle which causes acceleration and swirling of the fluid prior to its dispensing from the nozzle as a spray. Conventionally, the inner part of the nozzle provides a housing that defines an acceleration chamber and a separate shaped insert is provided to the chamber. The insert is shaped to cause the fluid to spin or swirl prior to it being dispensed from the tip and generally takes the form of a multi-bladed propeller-shaped swirl insert.

The Applicant has appreciated that the use of a separate swirl insert can give rise to certain manufacturing challenges. In particular, the performance of the swirl insert depends to an extent upon the accuracy of its fitting within the acceleration chamber. Variation in manufacturing tolerances in the shape and sizing of both the housing defining the acceleration chamber and the swirl insert can affect swirl performance as can variation in the fitting/location of the swirl insert within the chamber. Potential issues relating to manufacturing tolerances are only exacerbated by the small size of the swirl insert, which is typically sized to have a diameter of 2-3 millimeters. The Applicant has therefore realized the desirability of forming the housing and swirl insert as a composite part.

The Applicant has however, further appreciated that different challenges exist in forming the acceleration chamber and swirl insert as a single composite part. For mass production, moulding is the preferred manufacturing process, but the complex shaping of the inner (swirl) features of such a single composite part preclude the use of moulding as a manufacturing method. In essence, the problem is that it is impossible (or at least exceptionally difficult) to create a suitable mass production tool for moulding a single part that has the required inner acceleration/swirl features.

As a solution, the Applicant has therefore devised a composite part that may impart acceleration and swirl characteristics to a fluid wherein the composite part is defined by a mating assembly of like component parts. In particular, the composite part may be formed from two like mating halves or alternatively, from three like mating thirds, wherein each component part is shaped with both acceleration and swirl creating features. Preferably, the overall composite part defines an essentially cylindrical form such that each mating half of the two-part form defines a 180° segment of the cylinder or alternatively, each mating third of the three-part form defines a 120° segment of the cylinder.

It is an object of this invention to provide a nozzle for use in a fluid dispensing device that provides effective spraying from the nozzle.

It is a further object of this invention to provide a nozzle for use in a fluid dispensing device that on manufacture does not require the bringing together of separate acceleration chamber housing and swirl insert parts.

Applicant's co-pending PCT Patent Application No. WO 2004/094068 describes a nasal dispensing nozzle comprising a body defining a fluid flow channel; an inlet port defining an inlet to said channel, the inlet port shaped for receipt of said discharge outlet to enable delivery of said pumped fluid medicament to the channel; and an outlet port defining an outlet from said channel, the outlet port shaped for insertion into the nasal cavity of a user to enable delivery of the pumped fluid medicament thereto. A screw thread path is provided to the channel between the inlet and said outlet to impart angular momentum to the pumped fluid medicament.

SUMMARY ON THE INVENTION

According to one aspect of the present invention there is provided a nasal dispensing nozzle for use with a fluid medicament discharge pump device having a discharge outlet for discharge of pumped fluid medicament, the nasal dispensing nozzle comprising a body defining a fluid flow channel;

an inlet port defining an inlet to said channel, said inlet port shaped for receipt of said discharge outlet to enable delivery of said pumped fluid medicament to the channel; and an outlet port defining an outlet from the channel, wherein the channel is shaped to impart acceleration and angular momentum to the pumped fluid medicament, and wherein the body is comprised of a mating assembly of like component parts.

The term acceleration herein is used to have its conventional meaning of speeding up. The term angular momentum is meant to encompass the terms spin and/or swirl and may occur in either a clockwise or anti-clockwise sense. In the nozzle herein, the pumped fluid medicament experiences acceleration and spin/swirl as a result of its experience of being pumped through the channel (from the inlet to the outlet).

The present invention provides a nozzle for use with a nasal dispensing device for use in dispensing fluid form medicament to the nasal cavity of a user. The nozzle generally forms a component (either separable or integral) of a fluid medicament dispensing device, and the present invention therefore also provides a fluid medicament dispensing device incorporating the nozzle herein.

The nozzle is suitable for use with a fluid medicament discharge pump device having a discharge outlet for discharge of pumped fluid medicament. The fluid medicament discharge pump is generally comprised within a fluid medicament dispensing device as an integral or separable part thereof.

The nasal dispensing nozzle comprises a body defining a fluid flow channel. In use, the channel acts to guide the flow of fluid form medicament through the nozzle for dispensing therefrom. Embodiments are envisaged which comprise plural fluid flow channels (e.g. from two to five, preferably from two to three fluid flow channels). Each fluid flow channel is suitably defined as an enclosed volume (i.e. space) within the body.

The exterior of the body is generally shaped for engagement with a suitable fluid medicament discharge pump device (e.g. incorporated within a fluid medicament dispensing device).

The body is provided with an inlet port defining an inlet to the fluid flow channel. The inlet port is shaped for receipt of the discharge outlet of a fluid discharge pump device to enable delivery of pumped fluid medicament to the channel.

The body is also provided with an outlet port defining an outlet from the fluid flow channel for dispensing there from. The outlet port, which generally takes the form of a tip to the nozzle may be shaped for insertion into the nasal cavity of a user to enable delivery of the pumped fluid medicament thereto.

Suitably, the exterior of the body is shaped to define an overall cylindrical profile (i.e. it is in the form of a cylinder). Thus, the nasal dispensing device with which it is to be used suitably defines a cavity of corresponding cylindrical inner profile for receipt of the body of the nozzle.

The fluid flow channel is shaped to impart acceleration and angular momentum to the pumped fluid medicament.

Suitably, the fluid flow channel defines a screw path. That is to say, it has the general (i.e. helical) form of a screw, which may follow either a clockwise or anti-clockwise screw path direction. The path generally comprises from half to five complete (i.e. 360°) screw turns, which a fluid will experience as it travels from the inlet to the outlet.

The screw path generally extends in symmetric fashion about a defined screw axis. Suitably, the screw axis corresponds to the pumping axis defined by the pump of the fluid discharge device. Suitably, the fluid flow channel defined by the body of the nozzle is also symmetric about the screw axis. Suitably, the body of the nozzle further has an overall form that is symmetric about the screw axis, for example defining a cylindrical form about the screw axis.

The body may define a single screw path. In other aspects however, multiple screw paths are defined, wherein generally each is arranged about a single (i.e. common) screw axis and in complementary fashion to the other. Typically, from two to five, particularly from two to three threaded screw paths are defined. The number of screw paths may correspond to the number of like component parts of the mating assembly that defines the body.

Preferably, the flow path of the fluid flow channel is arranged decrease in cross-sectional area from the entrance thereto (i.e. at the inlet) to the exit thereto (i.e. at the outlet). The volume available to the fluid pumped there through progressively decreases and acceleration of the flow of the fluid therefore results. The decrease in cross-sectional area from entrance to exit may be achieved by progressively reducing the effective diameter of the fluid flow channel. In one aspect, the decrease in cross-sectional area is achieved by tapering the fluid flow channel.

The body of the nozzle herein is comprised of a mating assembly of like component parts. The body thus, comprises a composite part formed when the component parts thereof are brought together in mating fashion as an assembly. Each like component part is shaped to define part of the fluid flow channel and to provide both acceleration and angular momentum imparting features to that channel.

By like component parts it is meant that each component part has a similar overall form such that an assembly may be formed. The component parts are in one aspect, configured as mirror images, one of the other.

Suitably, the mating assembly that defines the body is formed from two mating halves or alternatively, from three mating thirds.

Preferably, the mating assembly that defines the body defines an essentially cylindrical form such that each mating half of the two-part form defines a 180° segment of the cylinder or alternatively, each mating third of the three-part form defines a 120° segment of the cylinder. Corresponding four (90°) and five (72°) part assemblies may also be envisaged, although it will be appreciated that increasing the number of component parts increases the complexity of assembly of the overall composite part.

Preferably, each like component part is amenable to manufacture by a moulding process such as an injection moulding process. Preferably, each like component part is comprised of a polymeric material that may be readily moulded. Moulding tools suitable for the manufacture of the like component parts form another aspect of the invention described herein.

Suitably, the body further defines a shaped outlet locating upstream of the fluid flow channel. Thus, the spinning and/or swirling fluid is delivered to the shaped outlet prior to its delivery in use, to the nasal cavity of the user. The shaped outlet is suitably arranged to define a tapered (e.g. fanned out) profile.

In one aspect, the outlet (e.g. shaped outlet) of the dispensing nozzle is provided with a reversible stopper. The stopper acts such as to prevent drain back of delivered fluid from the dispensing nozzle (in particular, from the area at the tip of the nozzle and generally adjacent to the dispensing outlet). The stopper is reversibly mountable to the nozzle (e.g. at the tip) and may have any suitable shape including disc shaped, wherein the disc may be flat, or in aspects have a convex or concave form.

It will be appreciated that the stopper is generally shaped for effective sealing engagement with the outlet of the dispensing nozzle (i.e. that area proximal to the dispensing orifice) and therefore that the shaping of the stopper may be arranged to inversely mirror that of the nozzle outlet.

The stopper may be formed from any suitable material including those with plastic properties, particularly those with resilient properties. Stoppers made from synthetic and naturally occurring polymers including rubber are herein envisaged.

According to another aspect of the present invention there is provided a housing assembly for reversible receipt of a fluid medicament discharge device for spraying a fluid medicament into a nasal cavity, the housing assembly comprising a housing defining a cavity; and engageable with said housing, a dispensing nozzle as described herein.

There is thus, also provided a fluid medicament dispensing device comprising a housing assembly as described above and received thereby, a fluid medicament discharge pump device.

In use, a fluid discharge device typically houses in the cavity, and in combination the housing assembly and fluid discharge device comprise a fluid dispensing device. Alternative embodiments are envisaged in which the fluid discharge device is either integral with or reversibly removable from the housing assembly of the fluid dispensing device.

The fluid discharge device typically has a hollow casing defining a reservoir for containing a volume of fluid and a pump having a suction inlet extending within the hollow casing, the pump having a discharge outlet extending from a first end of the hollow casing for co-operation with the dispensing nozzle to enable pumped delivery of fluid from the reservoir to the dispensing nozzle.

It will be appreciated that in general operation of the fluid discharge device relative movement between the hollow casing and the pump acts such as to pump fluid from the fluid reservoir into the dispensing nozzle for dispensing therefrom. The fluid reservoir typically contains several doses of fluid form medicament.

In aspects, the pumping is metered. For example, each pumping action results in delivery of a single dose of fluid from the reservoir to the nozzle.

Suitably for metered delivery, the pump includes a plunger, which is slideable in a metering chamber located within the hollow casing, the metering chamber being sized to accommodate a single dose of fluid.

Suitably, the pump comprises a pre-compression pump. Typically, such pre-compression pumps are used with a bottle (glass or plastic) capable of holding 8-50 ml of a formulation. Each spray will typically deliver 50-100 µl of such a formulation and the device is therefore capable of providing at least 100 metered doses.

The fluid medicament dispensing device may further comprise a protective end cap having an inner surface for engagement with the housing. The end cap is moveable from a first position in which it covers the nozzle to a second position in which the nozzle is uncovered.

In one aspect, a stopper locates on the end cap such that when the end cap is in the first (i.e. protective) position the stopper engages the nozzle to seal the nozzle orifice and thereby prevent drain back. In the second (i.e. in-use position) the stopper is disengaged from the nozzle such that the nozzle orifice is no longer sealed.

The stopper may form an integral part of the end cap or alternatively, the stopper may mount to the end cap. Any suitable method of mounting is envisaged including adhesive, snap-fit and weld mounting.

In general, the stopper locates in the inner part of the end cap. In one aspect, the inner part of the end cap is provided with annular walls defining a cavity for receipt of the stopper as an insert thereto. The stopper insert may be simply be mechanically inserted or it may be adhesively or otherwise fixed.

Suitable stopper insert forms may be formed in a variety of ways. In one aspect, a rubber disc-shaped stopper is stamped from a sheet of rubber. In another aspect, a disc-shaped stopper is moulded (e.g. by an injection moulding process). In a further aspect, the protective end cap is moulded and the stopper is then moulded within the formed end cap (i.e. a 'two shot' moulding process).

The hollow casing of the fluid medicament dispensing device may take any suitable form. Suitably, several lugs are formed on the hollow casing for engagement with complementary projections formed on the inner surface of the end cap, each of the lugs being arranged to extend through a longitudinally extending slot formed in the side wall of the body.

In one aspect, the hollow casing may have at least one outwardly extending detent for engagement with a complementary recess formed in the inner surface of the end cap so as to releasable hold the end cap in position on the body. Each detent may extend through a respective longitudinally extending slot in the body for engagement with the respective recess formed in the end cap.

According to a still further aspect of the present invention there is provided a kit of parts comprising a housing assembly as described above and a fluid discharge device receivable thereby. It is also envisaged that the housing assembly could be supplied as a separate item, into which a user or pharmacist later fits a suitable fluid discharge device.

It will be appreciated that whilst the present invention has been particularly described in terms of a nozzle suitable for delivery of fluid medicament to a nasal cavity, that variations of the invention are possible to enable delivery into other body cavities (e.g. the ear or eye).

BRIEF DESCRIPTION OF THE SEVERAL VIEWS OF THE DRAWINGS

The invention will now be described further with reference to the accompanying drawing in which:

FIG. 2 shows a perspective view of one like mating half of a first nozzle herein;

FIG. 6 shows a perspective view of one like mating third of a second nozzle herein;

DETAILED DESCRIPTION

Figure 1:
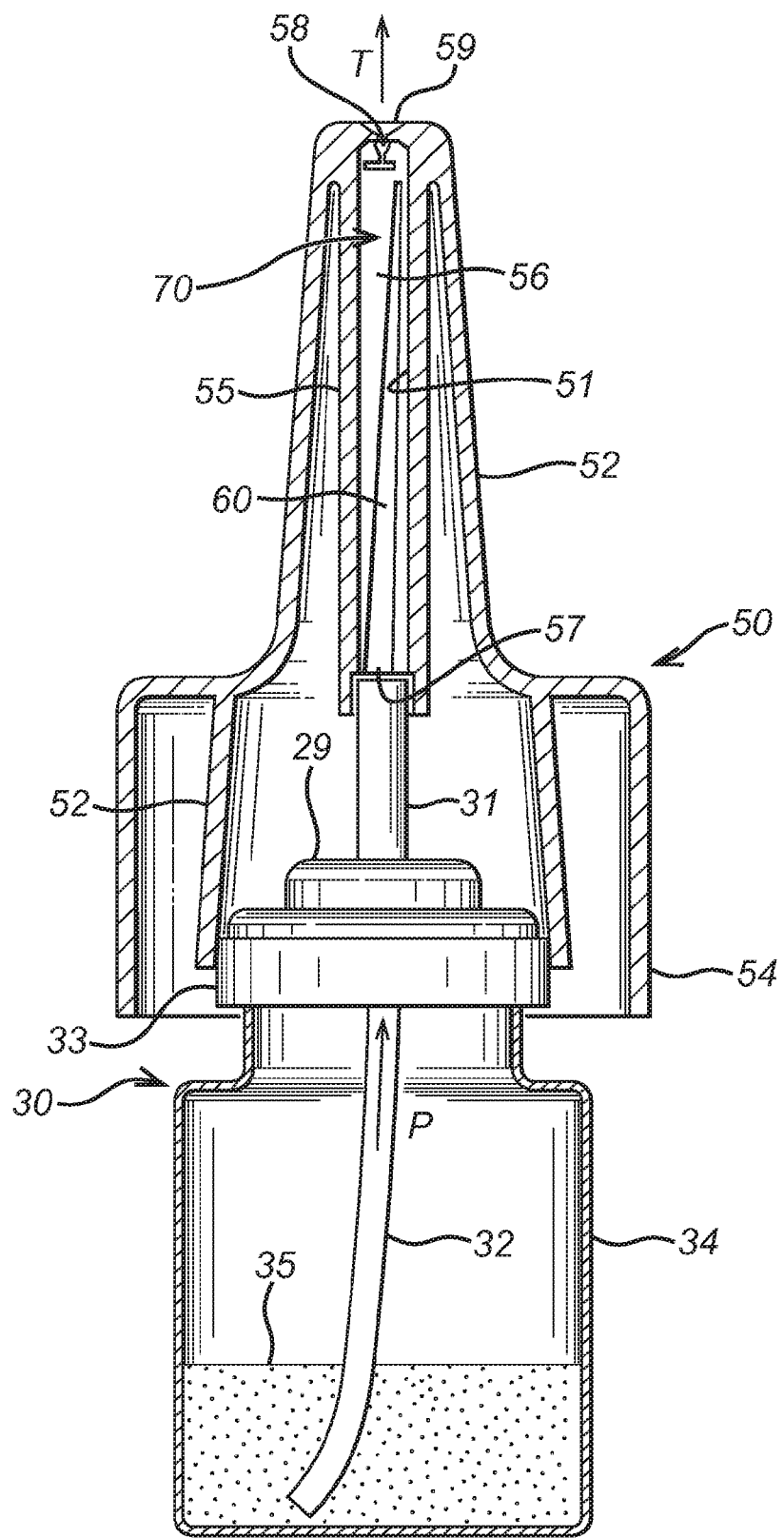
FIG. 1 is a cross-sectional view of a dispensing nozzle herein in engaging contact with a fluid medicament discharge pump device.
Figure 3A:
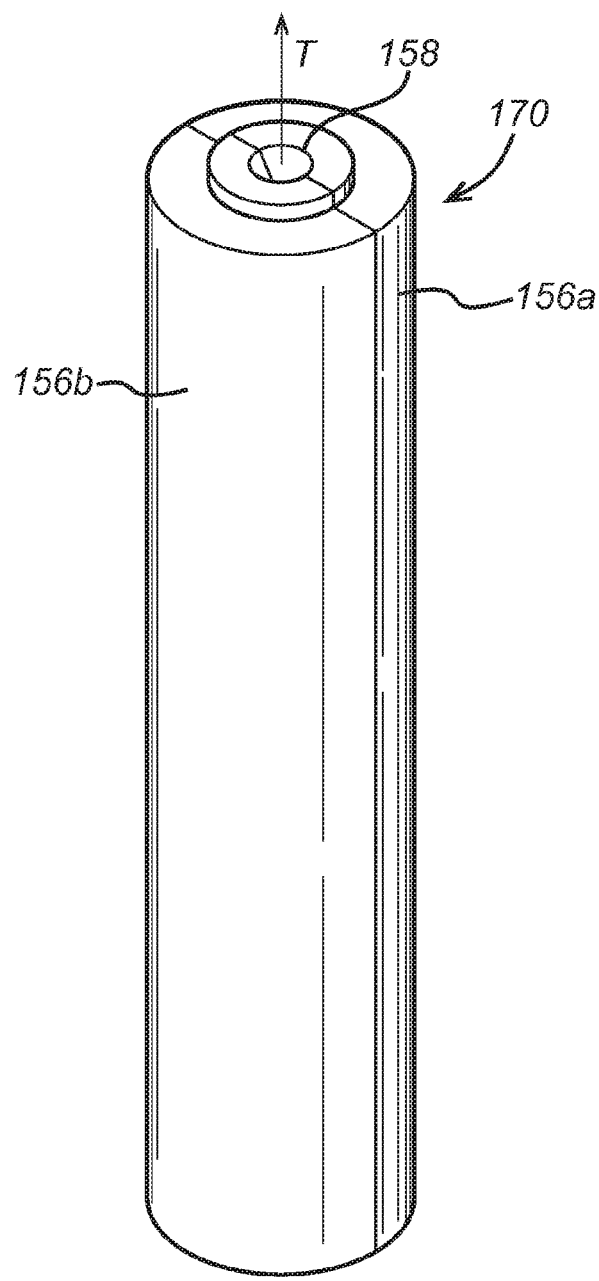
FIG. 3a shows a perspective view of the first nozzle herein formed by bringing together two like mating halves of the type as shown in FIG. 2.
Figure 3B:
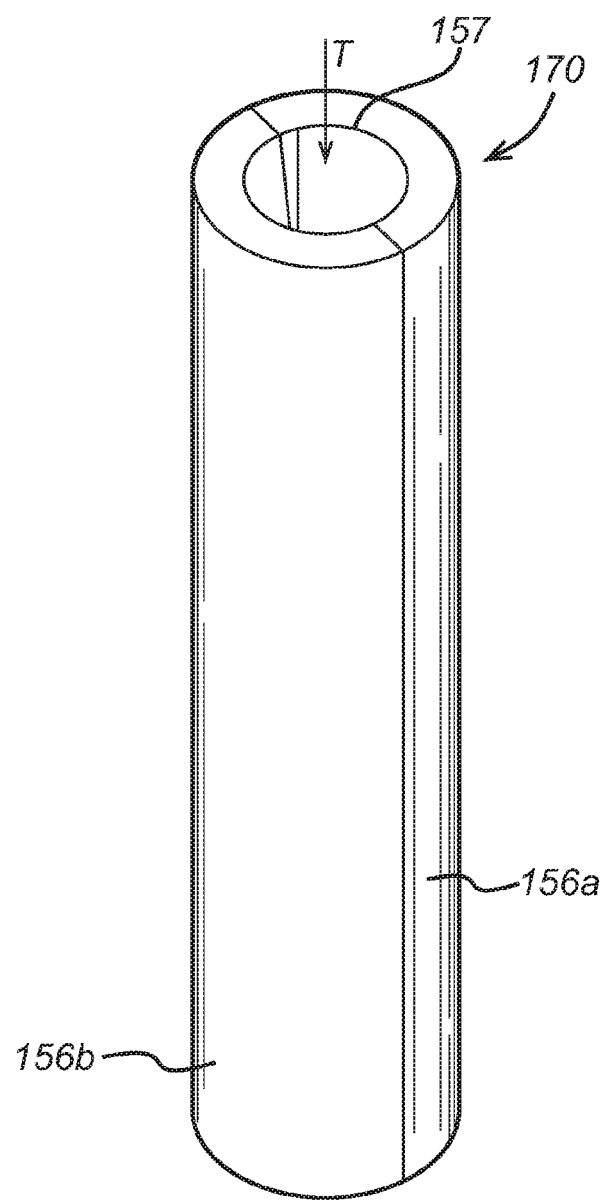
FIG. 3b shows a perspective view of the first nozzle of FIG. 3a as inverted to show the features of its lower end.

Referring now to the detail of the drawings, at FIG. 1 there is shown a dispensing nozzle housing 50 in engaging contact with a fluid medicament discharge pump device 30.

The fluid medicament discharge device 30 is of standard form and comprises a container 34 for storing the fluid form medicament 35 to be dispensed and a compression pump 29 having a suction inlet 32 located within the container 30 and a discharge outlet 31 for transferring fluid from the pump 29 to the nozzle housing 50. The compression pump 29 is actuable along a pumping axis designated 'P' in response to force applied to the container 34 to move it towards the nozzle housing 50 so as to compress the pump 29.

The nozzle housing 50 is provided with first cylindrical sleeve 52 for receiving collar 33 provided to the neck of the container 30. The nozzle housing 50 is also provided with a second cylindrical sleeve 54 concentric with the first cylindrical sleeve 52 and shaped for engagement with a second housing (not shown) for housing the fluid medicament discharge device 30.

Smooth cylindrical inner wall 55 of the nozzle housing 50 defines a cylindrical cavity 51 for receipt of cylindrical nozzle assembly 70 comprising body 56 that defines a progressively narrowing fluid flow channel 60 having a channel inlet 57 and tapering channel outlet 58. The tapering outlet 58 communicates with shaped outlet 59 of the cylindrical sleeve 52. It will also be seen that the channel inlet 57 communicates with the discharge outlet 31 of the fluid discharge pump device 30, which is in abutting contact therewith.

In use, the fluid medicament 35 is pumped from the container 34 via suction inlet 32 to discharge outlet 31 and thence, into the fluid flow channel 60 via the channel inlet 57. The inner structure of the body 56, which defines the fluid flow channel 60 will be better understood by reference to the later drawings of suitable nozzle assemblies 70, but for now it is noted that channel 60 defines a screw path having a screw thread axis 'T' such that pumped fluid medicament derives angular momentum there from before being dispensed from the dispensing outlet 58. The screw thread axis 'T' is arranged to be co-axial with pumping axis 'P'. Further, the aforementioned progressive narrowing of channel 60 imparts acceleration to the fluid medicament as it is pumped there through.

The characteristics of nozzles suitable for use with the fluid medicament dispensing device of FIG. 1 may be better understood by reference to FIGS. 2 to 5 and 6 to 9.

In more detail, FIGS. 2 to 5 show aspects of a first nozzle herein comprised of an assembly 170 of like mating body halves 156a, 156b. The assembly 170 has an overall cylindrical form such as would make it suitable for receipt by the cylindrical cavity 51 of the nozzle housing 50 of FIG. 1. Each mating body half 156a, 156b defines one half of a tapering, and hence progressively narrowing, fluid flow channel 160 having a channel inlet 157 and also a tapering channel outlet 158. In further detail, the fluid flow channel 160 may be seen to feed into inner chamber 162, which in turn feeds into chimney 164 that opens out into tapered dispensing outlet 158.

Figure 4:
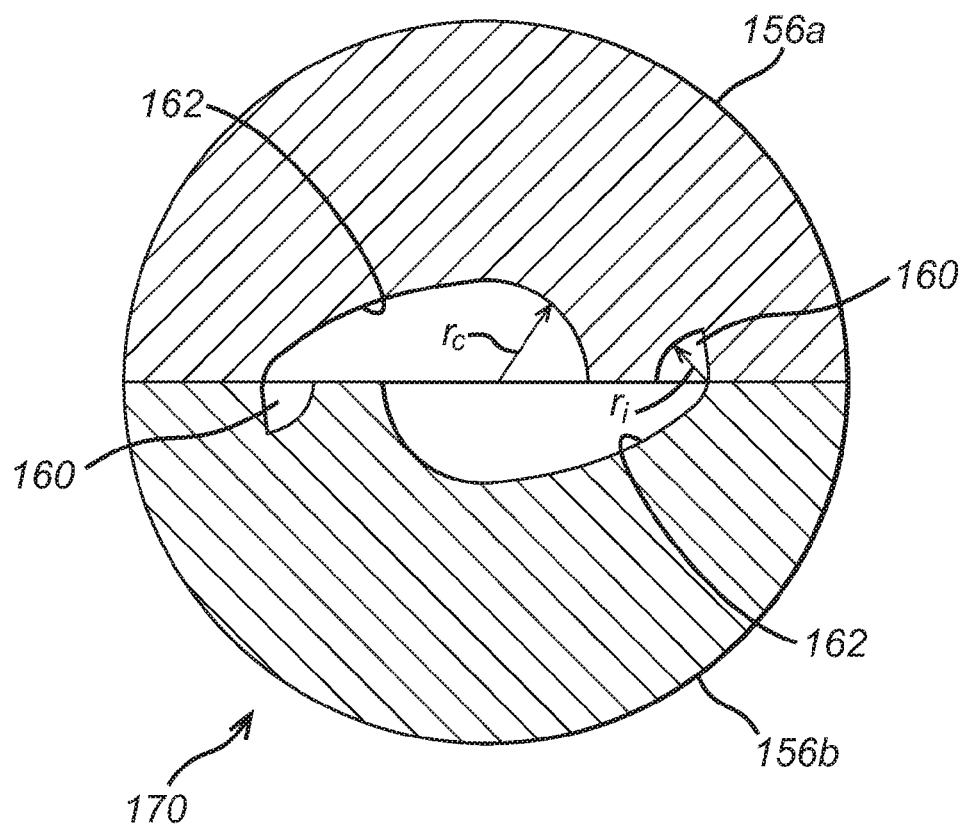
FIG. 4 shows a cross-sectional view of the first nozzle of FIG. 3a wherein for each like mating half thereof the cross-section is taken about plane X-X' of FIG. 2.

Referring now to the cross-sectional view of FIG. 4, the fluid flow channel 160 may be appreciated to define a screw path having a screw thread axis 'T' such as to impact angular momentum to fluid that is pumped from the channel inlet 157 via inner chamber 162 and chimney 164 to the dispensing outlet 158. The particular shape and form of inner chamber 162 may be seen by reference to FIG. 4.

Figure 5:
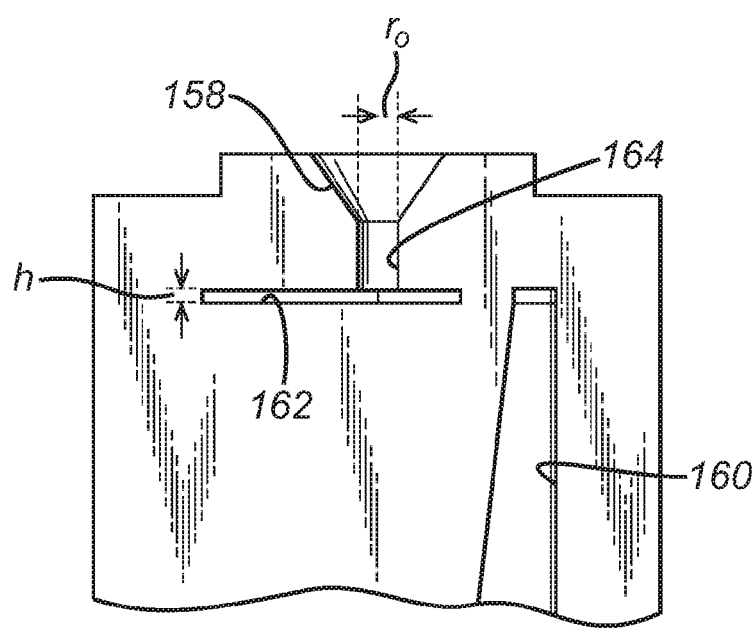
FIG. 5 shows a side view of details of the top part of the like mating half of FIG. 2.
Figure 7A:
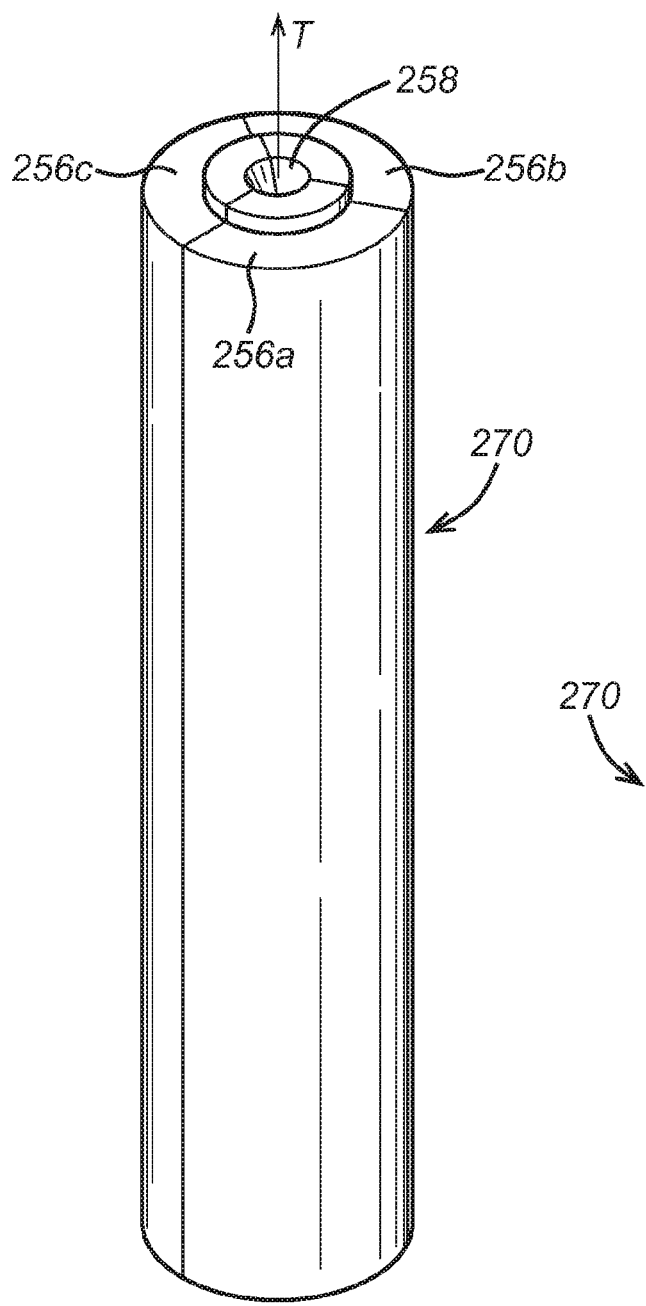
FIG. 7a shows a perspective view of the second nozzle herein formed by bringing together three like mating thirds of the type as shown in FIG. 6.
Figure 7B:
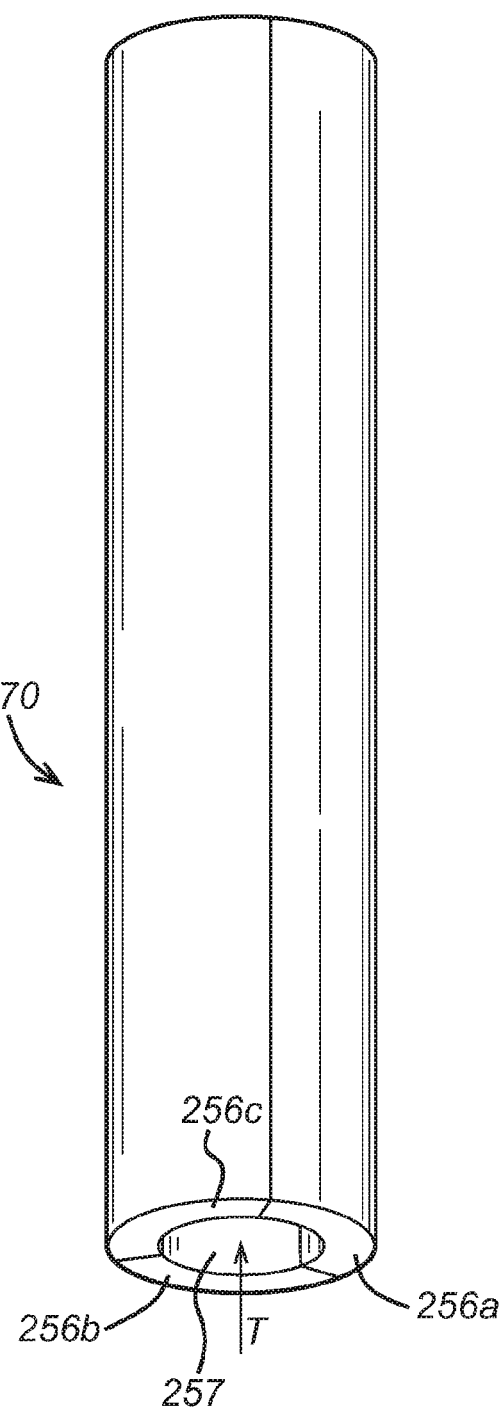
FIG. 7b shows a perspective view of the second nozzle of FIG. 7a as tilted to show the features of its lower end.

The Applicant has appreciated that the dispensing performance of the first nozzle of FIGS. 2 to 5 may be fine tuned by varying certain structural parameters thereof. In particular and as best seen in FIG. 4, first radius ($r_i$) and second radius ($r_c$) of the screw thread form dispensing channel 160 may be varied. Additionally and as best seen in FIG. 5, the height (h) of inner chamber 162 and the radius ($r_o$) of the chimney feed 164 to the tapering channel outlet 158 may be varied.

Turning now to FIGS. 6 to 9, there are shown aspects of a second nozzle herein comprised of an assembly 270 of like mating body thirds 256a, 256b, 256c. Again, the assembly 270 has an overall cylindrical form such as would make it suitable for receipt by the cylindrical cavity 51 of the nozzle housing 50 of FIG. 1. Each mating body third 156a, 156b, 256c defines one third of a tapering, and hence progressively narrowing, fluid flow channel 260 having a channel inlet 257 and also a tapering channel outlet 258. In further detail, the fluid flow channel 260 may be seen to feed into inner chamber 262, which in turn feeds into chimney 264 that opens out into tapered dispensing outlet 258.

Figure 8:
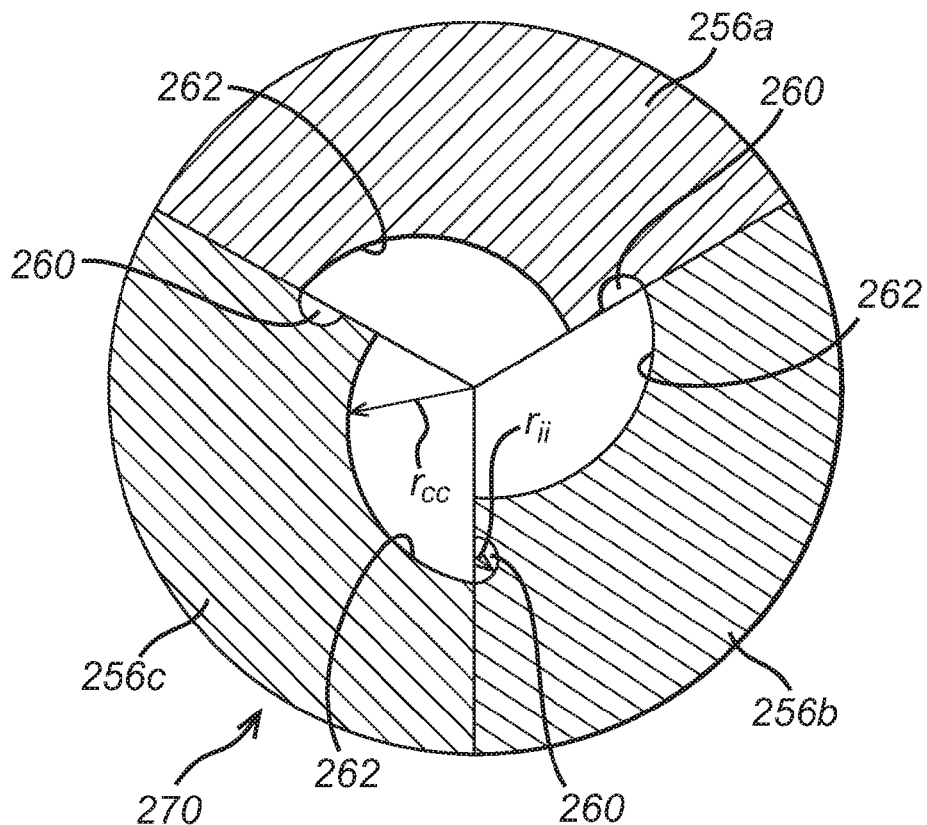
FIG. 8 shows a cross-sectional view of the second nozzle of FIG. 7a wherein for each like mating third thereof the cross-section is taken about plane Y-Y' of FIG. 6.

Referring now to the cross-sectional view of FIG. 8, the fluid flow channel 260 may be appreciated to define a screw path having a screw thread axis 'T' such as to impact angular momentum to fluid that is pumped from the channel inlet 257 via inner chamber 262 and chimney 264 to the dispensing outlet 258. The particular shape and form of inner chamber 262 may be seen by reference to FIG. 4.

Figure 9:
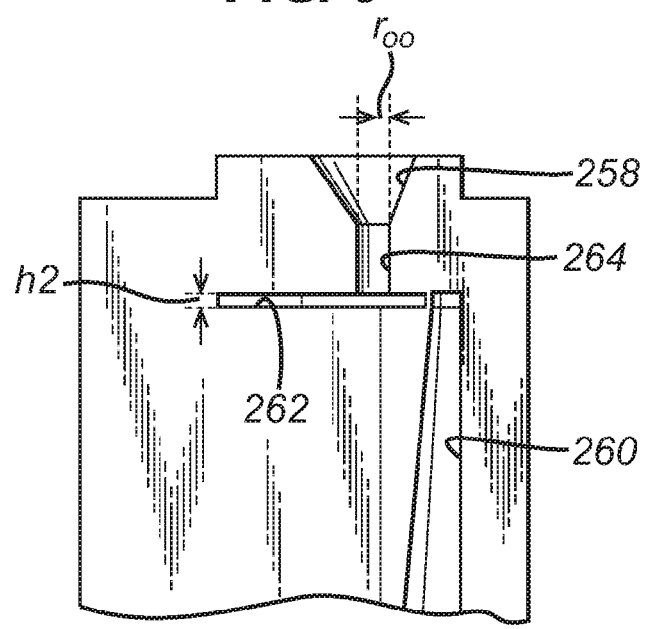
FIG. 9 shows a side view of details of the top part of the like mating third of FIG. 6.

As for the first nozzle, the Applicant has appreciated that the dispensing performance of the second nozzle of FIGS. 6 to 9 may be fine tuned by varying certain corresponding structural parameters thereof. In particular and as best seen in FIG. 8, first radius ($r_{ii}$) and second radius ($r_{cc}$) of the screw thread form dispensing channel 260 may be varied. Additionally and as best seen in FIG. 9, the height (h2) of inner chamber 262 and the radius ($r_{oo}$) of the chimney feed 264 to the tapering channel outlet 258 may be varied.

Administration of medicament may be indicated for the treatment of mild, moderate or severe acute or chronic symptoms or for prophylactic treatment. It will be appreciated that the precise dose administered will depend on the age and condition of the patient, the particular medicament used and the frequency of administration and will ultimately be at the discretion of the attendant physician. When combinations of medicaments are employed the dose of each component of the combination will in general be that employed for each component when used alone.

The fluid dispensing device herein is particularly suitable for dispensing a fluid medicament formulation. The container therefore contains a fluid medicament formulation e.g. formulated either as a solution formulation or as a suspension formulation comprising a suspension of active medicament particles in an inert suspending formulation.

Appropriate medicaments may thus be selected from, for example, analgesics, e.g., codeine, dihydromorphine, ergotamine, fentanyl or morphine; anginal preparations, e.g., diltiazem; antiallergics, e.g., cromoglycate (eg as the sodium salt), ketotifen or nedocromil (eg as the sodium salt); antiinfectives e.g., cephalosporins, penicillins, streptomycin, sulphonamides, tetracyclines and pentamidine; antihistamines, e.g., methapyrilene; anti-inflammatories, e.g., beclomethasone (eg as the dipropionate ester), fluticasone (eg as the propionate ester), flunisolide, budesonide, rofleponide, mometasone (eg as the furoate ester), ciclesonide, triamcinolone (eg as the acetonide), 6α, 9α-difluoro-11β-hydroxy-16α-methyl-3-oxo-17α-propionyloxy-androsta-1,4-diene-17β-carbothioic acid S-(2-oxo-tetrahydro-furan-3-yl) ester or 6α, 9α-Difluoro-17α-[(2-furanylcarbonyl)oxy]-11β-hydroxy-16α-methyl-3-oxo-androsta-1,4-diene-17β-carbothioic acid S-fluoromethyl ester; antitussives, e.g., noscapine; bronchodilators, e.g., albuterol (eg as free base or sulphate), salmeterol (eg as xinafoate), ephedrine, adrenaline, fenoterol (eg as hydrobromide), formoterol (eg as fumarate), isoprenaline, metaproterenol, phenylephrine, phenylpropanolamine, pirbuterol (eg as acetate), reproterol (eg as hydrochloride), rimiterol, terbutaline (eg as sulphate), isoetharine, tulobuterol or 4-hydroxy-7-[2-[[2-[[3-(2-phenylethoxy)propyl]sulfonyl] ethyl]amino]ethyl-2(3H)-benzothiazolone; PDE4 inhibitors eg cilomilast or roflumilast; leukotriene antagonists eg montelukast, pranlukast and zafirlukast; [adenosine 2a agonists, eg 2R,3R,4S,5R)-2-[6-Amino-2-(1S-hydroxymethyl-2-phenyl-ethylamino)-purin-9-yl]-5-(2-ethyl-2H-tetrazol-5-yl)-tetrahydro-furan-3,4-diol (e.g. as maleate)]*; [α4 integrin inhibitors eg (2S)-3-[4-({[4-(aminocarbonyl)-1-piperidinyl]

carbonyl}oxy)phenyl]-2-[((2S)-4-methyl-2-{[2-(2-methylphenoxy)acetyl]amino}pentanoyl)amino] propanoic acid (e.g as free acid or potassium salt)]*, diuretics, e.g., amiloride; anticholinergics, e.g., ipratropium (eg as bromide), tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagons. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament and/or to minimise the solubility of the medicament in the propellant.

Preferably, the medicament is an anti-inflammatory compound for the treatment of inflammatory disorders or diseases such as asthma and rhinitis.

In one aspect, the medicament is a glucocorticoid compound, which has anti-inflammatory properties. One suitable glucocorticoid compound has the chemical name: 6α, 9α-Difluoro-17α-(1-oxopropoxy)-11β-hydroxy-16α-methyl-3-oxo-androsta-1,4-diene-17β-carbothioic acid S-fluoromethyl ester (fluticasone propionate). Another suitable glucocorticoid compound has the chemical name: 6α, 9α-difluoro-17α-[(2-furanylcarbonyl)oxy]-11β-hydroxy-16α-methyl-3-oxo-androsta-1,4-diene-17β-carbothioic acid S-fluoromethyl ester. A further suitable glucocorticoid compound has the chemical name: 6α,9α-Difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester.

Other suitable anti-inflammatory compounds include NSAIDs e.g. PDE4 inhibitors, leukotriene antagonists, iNOS inhibitors, tryptase and elastase inhibitors, beta-2 integrin antagonists and adenosine 2a agonists.

The medicament is suitably in particulate form. The particulate medicament suitably has a mass mean diameter (MMD) of less than 20 μm, preferably between 0.5-10 μm, especially between 1-5 μm. If particle size reduction is necessary, this may be achieved by techniques such as micronisation, wet bead milling and/or microfluidisation.

Suitable medicament particles may be produced by conventional techniques, for example by micronisation, milling or sieving. Additionally, medicament and/or excipient powders may be engineered with particular densities, size ranges, or characteristics. Particles may comprise active agents, surfactants, wall forming materials, or other components considered desirable by those of ordinary skill.

In one aspect, the fluid medicament formulation is formulated as a medicament suspension formulation comprising a suspension of active medicament particles in an inert suspending formulation, optionally containing other pharmaceutically acceptable additive components.

The inert suspending formulation is typically aqueous and comprises one or more excipients. By the term "excipient", herein, is meant substantially inert materials that are non-toxic and do not interact with other components of a composition in a deleterious manner including, but not limited to, pharmaceutical grades of carbohydrates, organic and inorganic salts, polymers, amino acids, phospholipids, wetting agents, emulsifiers, surfactants, poloxamers, pluronics, and ion exchange resins, thixotropic agents and combinations thereof.

Suitable carbohydrates include monosaccharides including fructose; disaccharides, such as, but not limited to lactose, and combinations and derivatives thereof; polysaccharides, such as, but not limited to, cellulose and combinations and derivatives thereof; oligosaccharides, such as, but not limited to, dextrins, and combinations and derivatives thereof; polyols, such as but not limited to sorbitol, and combinations and derivatives thereof.

Suitable organic and inorganic salts include sodium or calcium phosphates, magnesium stearate, and combinations and derivatives thereof.

Suitable polymers include natural biodegradable protein polymers, including, but not limited to, gelatin and combinations and derivatives thereof; natural biodegradable polysaccharide polymers, including, but not limited to, chitin and starch, crosslinked starch and combinations and derivatives thereof; semisynthetic biodegradable polymers, including, but not limited to, derivatives of chitosan; and synthetic biodegradable polymers, including, but not limited to, polyethylene glycols (PEG), polylactic acid (PLA), synthetic polymers including but not limited to polyvinyl alcohol and combinations and derivatives thereof;

Suitable amino acids include non-polar amino acids, such as leucine and combinations and derivatives thereof. Suitable phospholipids include lecithins and combinations and derivatives thereof.

Suitable wetting agents, surfactants and/or emulsifiers include gum acacia, cholesterol, fatty acids including combinations and derivatives thereof. Suitable poloxamers and/or Pluronics include poloxamer 188, Pluronic® F-108, and combinations and derivations thereof. Suitable ion exchange resins include amberlite IR120 and combinations and derivatives thereof;

Preferred suspension formulations herein comprise an aqueous suspension of particulate medicament and one or more additional components selected from the group consisting of suspending agents, preservatives, wetting agents, viscosity enhancing agents and isotonicity adjusting agents.

Suitable suspending agents include carboxymethylcellulose, veegum, tragacanth, bentonite, methylcellulose and polyethylene glycols.

Particular suspending agents are those sold under the trade name Miglyol by Condea Chemie GmbH which comprise ester oils of saturated coconut and palm oil-derived caprylic and capric fatty acids and glycerin or propylene glycol. Particular examples include Miglyol 810, Miglyol 812 (caprylic/capric triglyceride); Miglyol 818 (caprylic/capric/linoleic triglyceride); Miglyol 829 (caprylic/capric/succinic triglyceride); and Miglyol 840 (propylene glycol dicaprylate/dicaprate).

Suitable preservatives include quaternary ammonium compounds (e.g. benzalkonium chloride, benzethonium chloride, cetrimide and cetylpyridinium chloride), mercurial agents (e.g. phenylmercuric nitrate, phenylmercuric acetate and thimerosal), alcoholic agents (e.g. chlorobutanol, phenylethyl alcohol and benzyl alcohol), antibacterial esters (e.g. esters of para-hydroxybenzoic acid), chelating agents such as disodium edetate (EDTA) and other anti-microbial agents such as chlorhexidine, chlorocresol, sorbic acid and its salts and polymyxin.

Suitable wetting agents function to wet the particles of medicament to facilitate dispersion thereof in the aqueous phase of the composition. Examples of wetting agents that can be used are fatty alcohols, esters and ethers. Preferably, the wetting agent is a hydrophilic, non-ionic surfactant, most preferably polyoxyethylene (20) sorbitan monooleate (supplied as the branded product Polysorbate 80).

Suitable viscosity enhancing agents include carboxymethylcellulose, veegum, tragacanth, bentonite, hydroxypropylmethylcellulose, hydroxypropylcellulose, hydroxyethylcellulose, poloxamers (eg. poloxamer 407), polyethylene glycols, alginates xanthym gums, carageenans and carbopols.

Suitable isotonicity adjusting agents act such as to achieve isotonicity with body fluids (e.g. fluids of the nasal cavity), resulting in reduced levels of irritancy associated with many nasal formulations. Examples of suitable isotonicity adjusting agents are sodium chloride, dextrose and calcium chloride.

Suitable thixotropic agents include that sold under the trade name Avicel RC951 NF, which comprises a mixture of carboxymethylcellulose sodium salt (8.3% to 13.8%) and microcrystalline cellulose. Thixotropic agents tend to make the formulation more viscous when static, but to become less viscous when kinetic energy is applied (e.g. on shaking the container).

In another aspect, the fluid medicament formulation is formulated as a solution medicament formulation. The formulation may be an aqueous, or in particular embodiments, a non-aqueous formulation. Suitable solution formulations may comprise a solubilising agent such as a surfactant.

Suitable surfactants include α-[4-(1,1,3,3-tetramethylbutyl)phenyl]-ω-hydroxypoly(oxy-1,2-ethanediyl) polymers including those of the Triton series e.g. Triton X-100, Triton X-114 and Triton X-305 in which the X number is broadly indicative of the average number of ethoxy repeating units in the polymer (typically around 7-70, particularly around 7-30 especially around 7-10) and 4-(1,1,3,3-tetramethylbutyl)phenol polymers with formaldehyde and oxirane such as those having a relative molecular weight of 3500-5000 especially 4000-4700, particularly Tyloxapol. The surfactant is typically employed in a concentration of around 0.5-10%, preferably around 2-5% w/w based on weight of formulation.

Suitable solution formulations may also comprise hydroxyl containing organic co-solvating agents include glycols such as polyethylene glycols (eg PEG 200) and propylene glycol; sugars such as dextrose; and ethanol. Dextrose and polyethylene glycol (eg PEG 200) are preferred, particularly dextrose. Propylene glycol is preferably used in an amount of no more than 20%, especially no more than 10% and is most preferably avoided altogether. Ethanol is preferably avoided. The hydroxyl containing organic co-solvating agents are typically employed at a concentration of 0.1-20% e.g. 0.5-10%, e.g. around 1-5% w/w based on weight of formulation.

Suitable solution formulations may also comprise solubilising agents such as polysorbate, glycerine, benzyl alcohol, polyoxyethylene castor oils derivatives, polyethylene glycol and polyoxyethylene alkyl ethers (e.g. Cremophors, Brij). Other solubilising agents are those sold under the trade name Miglyol by Condea Chemie GmbH which comprise ester oils of saturated coconut and palm oil-derived caprylic and capric fatty acids and glycerin or propylene glycol.

One non-aqueous solution formulation is based upon Miglyol (trade name) either used neat to solubilise the medicament substance, or as a mixture with propylene glycol and/or polyethylene glycol.

Suitable suspension or solution formulations may be stabilised (e.g. using hydrochloric acid or sodium hydroxide) by appropriate selection of pH.

Typically, the pH will be adjusted to between 4.5 and 7.5, preferably between 5.0 and 7.0, especially around 6 to 6.5.

The fluid medicament formulation herein suitably has a viscosity of from 10 to 2000 mPa.s (10 to 2000 centipoise), particularly from 20 to 1000 mPa.s (20 to 1000 centipoise), such as from 50 to 1000 mPa.s (50 to 1000 centipoise) at 25° C.

The viscosity of the inert suspending formulation herein is measured by any suitable method.

The dispensing device herein is suitable for dispensing fluid medicament formulations for the treatment of inflammatory and/or allergic conditions of the nasal passages such as rhinitis e.g. seasonal and perennial rhinitis as well as other local inflammatory conditions such as asthma, COPD and dermatitis.

A suitable dosing regime would be for the patient to inhale slowly through the nose subsequent to the nasal cavity being cleared. During inhalation the formulation would be applied to one nostril while the other is manually compressed. This procedure would then be repeated for the other nostril. Typically, one or two inhalations per nostril would be administered by the above procedure up to three times each day, ideally once daily. Each dose, for example, may deliver 5 µg, 50 µg, 100 µg, 200 µg or 250 µg of active medicament. The precise dosage is either known or readily ascertainable by those skilled in the art.

It will be understood that the present disclosure is for the purpose of illustration only and the invention extends to modifications, variations and improvements thereto.

The application of which this description and claims form part may be used as a basis for priority in respect of any subsequent application. The claims of such subsequent application may be directed to any feature or combination of features described therein. They may take the form of product, method or use claims and may include, by way of example and without limitation, one or more of the following claims.

What is claimed is:

1. A nozzle for use in a fluid dispensing device, the nozzle comprising:
    a body defining a fluid flow channel which is shaped to impart acceleration and angular momentum to fluid passing therethrough,
    an inlet port formed in the body and defining an inlet to said channel, and
    an outlet port formed in the body and defining an outlet from the channel,
    wherein the fluid flow channel includes a swirl chamber having a plurality of swirl chamber segments, the swirl chamber being located between the channel inlet and the channel outlet,
    wherein the body is comprised of a mating assembly of a plurality of like component parts, each of the component parts providing one of the swirl chamber segments;
    wherein the fluid flow channel includes a plurality of inlets to the swirl chamber for feeding fluid into the swirl chamber and wherein each of the component parts provides one of the swirl chamber inlets;
    wherein the swirl chamber inlets are positioned to feed fluid into respectively different swirl chamber segments and wherein the swirl chamber segments are fed from one of the swirl chamber inlets provided by another of the component parts; and
    wherein each swirl chamber inlet is connected to the channel inlet by a separate branch of the fluid flow channel.

2. A nozzle according to claim 1, wherein the body has a first end and a second end which is spaced in a longitudinal direction from the first end and wherein the components extend longitudinally from the first end to the second end.

3. A nozzle according to claim 2, wherein the inlet port is formed in the first end and the outlet port is formed in the second end.

4. A nozzle according to claim 3, wherein each of the component parts provides a segment of the inlet and outlet ports.

5. A nozzle according to claim 2, wherein the components have at least one longitudinal face in which at least one recess is formed, wherein the at least one longitudinal face of each component abuts with at least one longitudinal face of at least one other component, and wherein the recesses collectively define the fluid flow channel.

6. A nozzle according to claim 5, wherein the body is generally cylindrical, wherein the mating assembly has n component parts where n is a whole number of at least 2, and wherein each component part defines a 360°/n segment of the body.

7. A nozzle according to claim 6, wherein n=2 and the component parts are mating halves.

8. A nozzle according to claim 6, wherein n=3 and the component parts are mating thirds.

9. A nozzle according to claim 5, wherein the component parts are mating halves of the body.

10. A nozzle according to claim 1, wherein each branch is provided by a different component part.

11. A nozzle according to claim 1, wherein the branches narrow in cross-section in the direction from the channel inlet to the swirl chamber inlet.

12. A nozzle according to claim 1, wherein the fluid flow channel narrows in cross-section from the channel inlet to the swirl chamber inlets.

13. A nozzle according to claim 1, wherein the swirl chamber is disposed upstream from and in close proximity to the outlet port.

14. A nozzle according to claim 13, wherein the outlet port has a profile which tapers outwardly in the flow direction.

15. A nozzle according to claim 14, wherein the swirl chamber has a roof and wherein the fluid flow channel includes a chimney section which extends from the roof to the tapered profile of the outlet port.

16. A nozzle according to claim 1, wherein the component parts are moulded component parts.

17. A nozzle according to claim 1, wherein the component parts are identical.

18. A nozzle according to claim 1 which is shaped and sized for insertion into a nasal passage.

19. A nozzle according to claim 1, wherein the body is a sub-assembly of the nozzle.

20. A body for a nozzle for use in a fluid dispensing device, wherein the body defines
    a fluid flow channel which is shaped to impart acceleration and angular momentum to fluid passing therethrough;
    an inlet port formed in the body and defining an inlet to said channel; and
    an outlet port formed in the body and defining an outlet from the channel,
        wherein the fluid flow channel includes a swirl chamber having a plurality of swirl chamber segments, the swirl chamber being located between the channel inlet and the channel outlet,
        wherein the body is comprised of a mating assembly of a plurality of like component parts, each of the component parts providing one of the swirl chamber segments,
        wherein the fluid flow channel includes a plurality of inlets to the swirl chamber for feeding fluid into the swirl chamber and wherein each of the component parts provides one of the swirl chamber inlets;
        wherein the swirl chamber inlets are positioned to feed fluid into respectively different swirl chamber segments and wherein the swirl chamber segments are fed from one of the swirl chamber inlets provided by another of the component parts, and
        wherein each swirl chamber inlet is connected to the channel inlet by a separate branch of the fluid flow channel.

* * * * *